(12) United States Patent
Burkinshaw

(10) Patent No.: US 6,960,214 B2
(45) Date of Patent: Nov. 1, 2005

(54) METHOD FOR PERFORMING AUTOMATED MICROFRACTURE

(75) Inventor: Brian Burkinshaw, Pflugerville, TX (US)

(73) Assignee: Zimmer Austin, Inc., Austin, TX (US)

( * ) Notice: Subject to any disclaimer, the term of this patent is extended or adjusted under 35 U.S.C. 154(b) by 233 days.

(21) Appl. No.: 10/348,507

(22) Filed: Jan. 21, 2003

(65) Prior Publication Data

US 2004/0073223 A1 Apr. 15, 2004

Related U.S. Application Data

(60) Provisional application No. 60/418,545, filed on Oct. 15, 2002.

(51) Int. Cl.$^7$ .............................................. A61B 17/00
(52) U.S. Cl. ....................................................... 606/79
(58) Field of Search ..................... 606/186, 79; 81/9.22

(56) References Cited

U.S. PATENT DOCUMENTS

| | | | | |
|---|---|---|---|---|
| 3,509,789 | A | * | 5/1970 | Buttner ........................ 81/9.22 |
| 4,031,783 | A | * | 6/1977 | Paul et al. ..................... 81/9.22 |
| 5,471,102 | A | * | 11/1995 | Becker et al. ................. 310/50 |
| 5,921,987 | A | * | 7/1999 | Stone .......................... 606/80 |
| 6,273,861 | B1 | | 8/2001 | Bates et al. |
| 6,475,193 | B1 | * | 11/2002 | Park ............................. 604/191 |
| 6,527,716 | B1 | * | 3/2003 | Eppstein ..................... 600/309 |
| 6,588,301 | B1 | * | 7/2003 | Chanet et al. ............... 81/9.22 |
| 2002/0072717 | A1 | * | 6/2002 | Mueller et al. ............. 604/212 |

OTHER PUBLICATIONS

Steadman, J. Richard; M.D.; Sulzer Orthopedics/Joint Care/Fracture Care; *Microfracturing Instrumentation Product Information and Operative Technique*, Sulzer Medica, 2001, 12 pages.
Electro Medical Systems; *Swiss OrthoClast*, 4 pages.
Saturn Orthopedics, *Accu-Jackson; Automated Osteotome System for Removal of Cement or Fixated Prosthesis*, 2 pages.
Arthrex, *Chondro Picks, 1998/99 Product Catalog*, 3 pages.

* cited by examiner

*Primary Examiner*—Pedro Philogene
(74) *Attorney, Agent, or Firm*—Williams, Morgan & Amerson, P.C.

(57) ABSTRACT

The present invention is directed to a method for repairing defects in articular cartilage and, more particularly, to a new method for performing automated microfracture on subchondral bone to repair articular cartilage. The microfractured holes on the surface of the subchondral bone plate are formed with an automated process using a pneumatically driven orthopedic microfracture instrument. The instrument moves a fracture pin through the end of a guide tube until a sharp end of the fracture pin punctures or penetrates the subchondral bone plate and creates a microfracture or hole in the bone.

20 Claims, 2 Drawing Sheets

METHOD FOR PERFORMING AUTOMATED MICROFRACTURE

CROSS-REFERENCE TO RELATED APPLICATIONS

This application claims benefit of priority of U.S. Provisional Application Ser. No. 60/418,545 filed Oct. 15, 2002.

FIELD OF THE INVENTION

The disclosure herein generally relates to a method for repairing defects in articular cartilage and, more particularly, to a new method for performing automated microfracture on subchondral bone to repair articular cartilage.

BACKGROUND OF THE INVENTION

Articular cartilage is a highly organized avascular tissue composed of chondrocytes formed in an extracellular matrix. This tissue is extremely important to the normal, healthy function and articulation of joints. Articular cartilage enables joint motion surfaces to articulate smoothly with a very low coefficient of friction. It also acts as a cushion to absorb compressive, tensile, and shearing forces and, thus, helps protect the ends of bone and surrounding tissue.

Injuries and defects to articular cartilage are frequent. Traumatic chondral injuries, for example, are common in sports and other activities that cause severe stress and strain to joints. Osteoarthritis is also a common condition that develops as cartilage wears, weakens, and deteriorates at the joint motion surfaces of bones.

Unfortunately, articular cartilage is generally thin with an extremely low or insignificant blood flow and, as such, has a very limited ability to repair or heal itself. Partial-thickness chondral defects, for example, cannot spontaneously heal. If these defects are left untreated, they often degenerate at the articular surface and progress to osteoarthritis. Full-thickness defects that penetrate subchondral bone can undergo some spontaneous repair if fibrocartilage forms at defect. Even in spite of the formation of fibrocartilage, clinical evidence shows that full-thickness defects continue to degenerate and progress to osteoarthritis if these defects are left untreated.

Early diagnosis and treatment are crucial to hindering or stopping the progression of arthritis and degeneration of articular cartilage at joint motion surfaces. Today, depending on the grade of chondral damage, patients usually have several surgical options to repair or regenerate articular cartilage.

For small injuries, such as partial-thickness defects, a patient can be treated with a palliative procedure using known lavage and debridement techniques. These techniques remove loose debris and smooth shredded or frayed articular cartilage. Although this arthroscopic technique is common, relief for the patient can be incomplete and temporary.

Osteochondral autologous transplantation (OATS) and autologous chondrocyte implantation (ACI) are two other treatment modalities used to treat larger or more severe articular defects.

In OATS, cartilage is removed from a normal, healthy location and transferred or planted to the defective area. This procedure is inherently limited to the amount or availability of healthy autologous osteochondral grafts in the patient. Spaces between graft plugs and lack of integration with donor and recipient hyaline cartilage are other clinical concerns with OATS.

In ACI, articular cartilage cells are arthroscopically removed or harvested from the patient and sent to a laboratory. Here, the cells are cultured and multiplied. The newly grown chondrocytes are then re-implanted back into the patient at the defected area. The process of growing cells outside the patient can be expensive. Further, this procedure can require a relatively larger incision to place the cartilage cells. What's more, several years may be required for the implanted cells to mature fully.

Microfracture is another treatment modality used to treat articular defects. This technique is a marrow stimulating arthroscopic procedure to penetrate the subchondral bone to induce fibrin clot formation and the migration of primitive stem cells from the bone marrow into the defective cartilage location. More particularly, the base of the defective area is shaved or scraped to induce bleeding. An arthroscopic awl or pick is then used to make small holes or microfractures in the subchondral bone plate. The end of the awl is manually struck with a mallet to form the holes while care is made not to penetrate too deeply and damage the subchondral plate. The holes penetrate a vascularisation zone and stimulate the formation of a fibrin clot containing pluripotential stem cells. The clot fills the defect and matures into fibrocartilage.

Microfracturing the subchondral bone plate can be a successful procedure for producing fibrocartilaginous tissue and repairing defective articular cartilage. The current procedure or method for performing the surgical technique, though, has some disadvantages.

As one disadvantage, the microfractures or holes are made when the surgeon manually strikes or otherwise forces the awl into the subchondral bone plate. Specifically, the holes are manually created. Manually created holes in the bone plate can have inconsistent depths depending on the force applied to the awl. If the holes are not deep enough, then the formation of the fibrin clot may not occur. On the other hand, if the holes are too deep, then the subchondral bone plate can be damaged and lead to unwanted consequences and complications. The depth of the holes, thus, depends on the skill of the surgeon to accurately and consistently hit the end of the awl and force it to the correct depth in the bone plate.

As another disadvantage, many microfractures may be placed in a single surgery. Each hole must be manually placed, and the creation of the many holes can take a lot of time during the surgery. Depending on the size of the defect being treated, 25–100 or more holes could be required. Several hours may be required to place manually each of these holes.

As yet another disadvantage, the microfractures should be placed 3 to 4 millimeters apart from each other on the bone plate. The placement of these holes and distance between adjacent holes, then, depends on the visual judgment and skill of the surgeon.

It therefore would be advantageous to provide a new method for performing the microfracture surgical technique. Such method would eliminate the disadvantages associated with conventional microfracture surgery.

SUMMARY OF THE INVENTION

The present invention is directed to a method for repairing defects in articular cartilage and, more particularly, to a new method for performing automated microfracture on subchondral bone to repair full thickness chondral defects. The important advantage of the present invention is that the microfractured holes on the surface of the subchondral bone plate are formed with an automated process. In particular, this automated process of the present invention uses a pneumatic, hydraulic, electric powered, or otherwise orthopedic gun or instrument to create the microfractures. The microfracture inserter generally comprises a body portion with a microfracture pin assembly removeably connected to the end of the body portion. The microfracture pin assembly generally includes a guide tube, a connector, a biasing member, and a fracture pin. The inserter forceably moves the fracture pin through the end of the guide tube until a sharp end of the fracture pin punctures or penetrates the subchondral bone plate and creates a microfracture or hole in the bone. The biasing member retracts the pin back into guide tube and positions the pin to complete another cycle.

Broadly described, the method is directed toward performing microfracture surgery on subchondral bone, and this method includes the steps of establishing arthroscopic access to the knee; identifying the chondral defect in the knee; debriding the subchondral bone at the chondral defect and creating a pool to receive the formation of a super-clot; providing an automated microfracture instrument; creating multiple holes in the subchondral bone with the automated microfracture instrument; penetrating the bone to sufficient depth to induce the formation of fat droplets; removing all instruments from the knee; and closing the arthroscopic access to the knee.

One important advantage of the present invention is that the microfractures are not manually made. Instead, the microfractures are formed with an automated orthopedic gun or instrument, such as an orthopedic microfracture inserter or instrument. The use of an automated instrument has many advantages over the prior method of manually forming the microfractures. The holes in the subchondral bone plate can be formed to have a consistent depth. Further, the depth of the holes can be controlled. Thus, the risk of penetrating too deeply into the bone plate is reduced or eliminated.

As another advantage, the microfractures are quickly created with the automated orthopedic instrument. A surgeon merely pulls a trigger, pushes a button, or steps on a control switch to activate movement of the fracture pin and create a microfracture in the bone plate. Successive microfractures are created with repeated activation of the instrument.

As yet another advantage, the holes can easily be spaced 3 to 4 millimeters apart from one another. The microfracture pin assembly also includes a mechanism to guide the placement of the holes.

DETAILED DESCRIPTION

Figure 1:
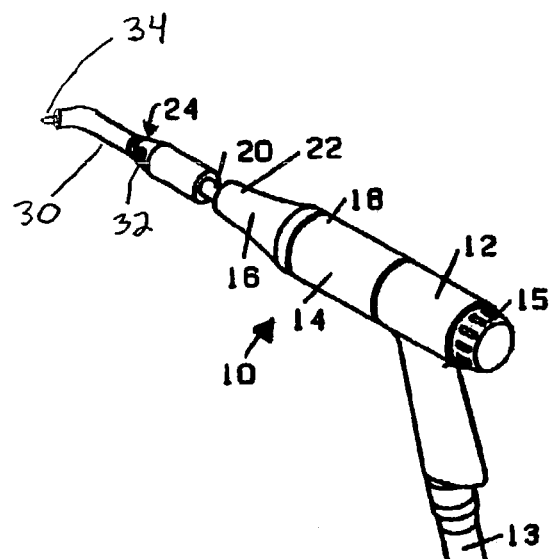
FIG. 1 is a perspective view of a pneumatically powered microfracture inserter that has a microfracture pin assembly of the present invention.

The instruments, method, and steps of the present invention are now described in more detail. The method describes the steps to perform an automated surgical microfracture procedure on subchondral bone to repair or regenerate articular cartilage at a full-thickness defect. Some of these steps described in the method are known to those skilled in the art and will not be discussed in great detail. Further, one skilled in the art will appreciate that certain steps may be altered or omitted while other steps may be added without departing from the scope of the invention.

Further, the novel microfracture method of the present invention will be described in connection with arthroscopic knee surgery; though one skilled in the art will appreciate that the microfracture method may be done as an "open" procedure as well. Specifically, the method will address a patient having unstable cartilage covering the underlying bone or a full-thickness defect (i.e., loss of articular cartilage down to the bone), for example, in either a weight bearing area of contact between the femur and tibia or in an area of contact between the back of the patella and the trochlear groove. One skilled in the art, though, will appreciate that the invention can be utilized at various other locations other than the knee to repair or regenerate articular cartilage.

To facilitate a discussion of the present invention, the method is divided into three different sections: Diagnostic Evaluation, Site Preparation, and Microfracture Technique and Instrumentation. Each of these sections is discussed seriatim.

Diagnostic Evaluation

Once on the operating table, the patient is placed in a supine position, and standard arthroscopic portals are made through the skin. Generally, two or more ports are made to provide access to the knee. An arthroscopic camera is used through one port, and other arthroscopic instrumentation are used through the other port or ports.

Any associated pathology, such as meniscal tears or loose body, should be addressed before the microfracture procedure. If no such conditions exist, a thorough diagnostic examination of the knee is performed. This examination should include an inspection of the suprapatellar pouch, the medial and lateral gutters, the patellofemoral joint, and the notch and its contents. Further, the examination can include the medial and lateral compartments and posterior horns of both menisci. Other intra-articular procedures and examinations, as deemed necessary, can also be included. A thorough examination may be helpful when a loss in visualization occurs after fat droplets and blood enter the knee from the microfractures.

Site Preparation

The next step is to identify visually the lesion or defect in the articular cartilage. The boundaries or limits of the defect should be clearly defined. Next, the exposed bone under the defect is debrided of cartilage tags. A curette and full radius resector or "Gator" shaver can be used for debridement. All loose or marginally attached cartilage from the surrounding rim of articular cartilage should be debrided to create a stable edge of healthy, viable cartilage around the defect.

The creation of an edge has an important purpose: It provides a pool or recess to receive the formation of a clot. Further, a curette may be used to remove the calcified layer of cartilage from the base of the defect. Removal of this calcified layer is important as it enhances the amount of defect that is ultimately filled. Removal of this layer also provides a more adequate surface for adherence of the clot and for improved chondral nutrition through subchondral diffusion. Additionally, care should be taken not to debride through the calcified layer to avoid excessive damage to the subchondral bone.

Microfracture Technique and Instrumentation

The important advantage of the present invention is that the microfractured holes on the surface of the subchondral bone plate are formed with an automated process. FIG. 1 shows a pneumatically driven orthopedic microfracture instrument or inserter 10. The microfracture inserter generally comprises a handle 12 to which an air hose 13 is attached. The handle 12 supports or connects to a cylinder impaction assembly 14 at one end and a flow control knob 15 at one another end. Control knob 15 is adapted to control and adjust the flow of air into handle 12 and impaction assembly 14. A nose assembly 16 connects to a distal end 18 of the impaction assembly. A shaft 20 protrudes from a distal end 22 of the nose assembly 16 and removeably connects to a microfracture pin assembly 24. This assembly 24 generally includes a guide tube 30, a connector 32, and a fracture pin 34.

The present invention centers around the microfracture pin assembly 24 and its use in microfracture surgical techniques. This assembly 24 can be attached to or used in conjunction with various types of automated orthopedic guns or instruments known in the art, such as pneumatic, hydraulic, or electric powered orthopedic guns and instruments. A pneumatically driven orthopedic gun (such as orthopedic microfracture inserter 10) is just one example. As such, the inner workings of the pneumatic microfracture inserter 10 are not discussed. Generally described though, pressured air is pumped via air hose 13 and into a manifold in housing 12. The manifold abuts an anvil or anvil plate. The manifold, anvil, valves, and other components function to move a cylinder or piston in the cylinder impaction assembly 14. This piston is driven with air pressure to impact against one end of the fracture pin 34. As the piston strikes the end, the fracture pin is guided along the inside of the guide tube 30 until a sharp end of the fracture pin moves outwardly, away from the end of the guide tube. This sharp end punctures or penetrates the subchondral bone plate and creates a microfracture or hole in the bone.

Figure 2:
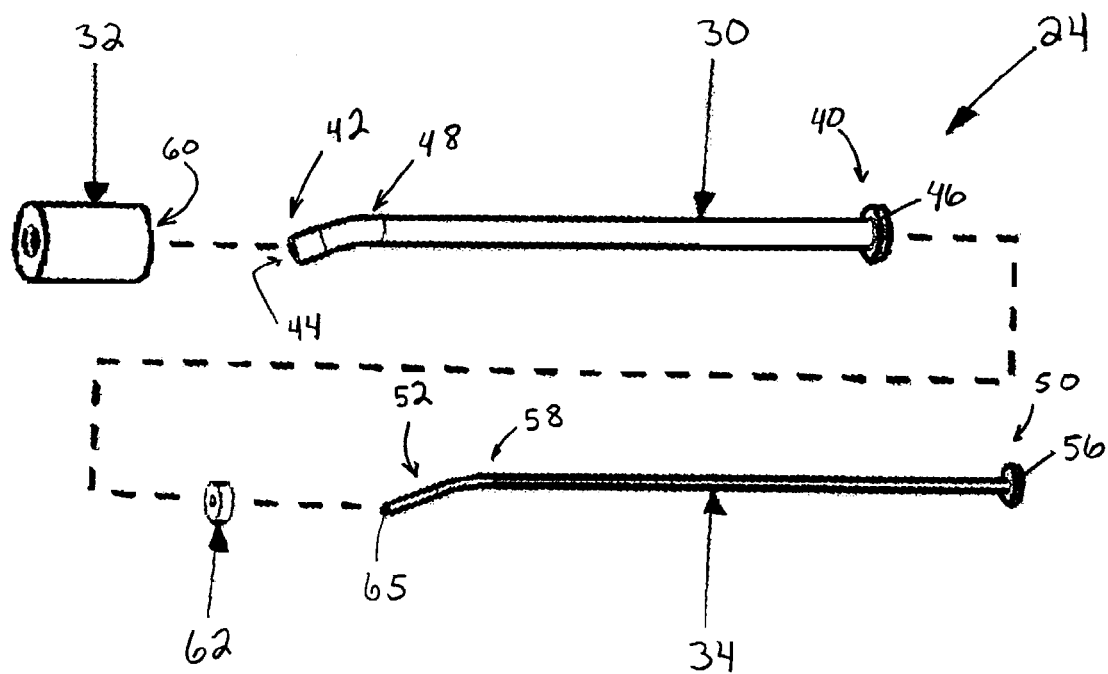
FIG. 2 is an exploded view of the microfracture pin assembly of FIG. 1.
Figure 3:
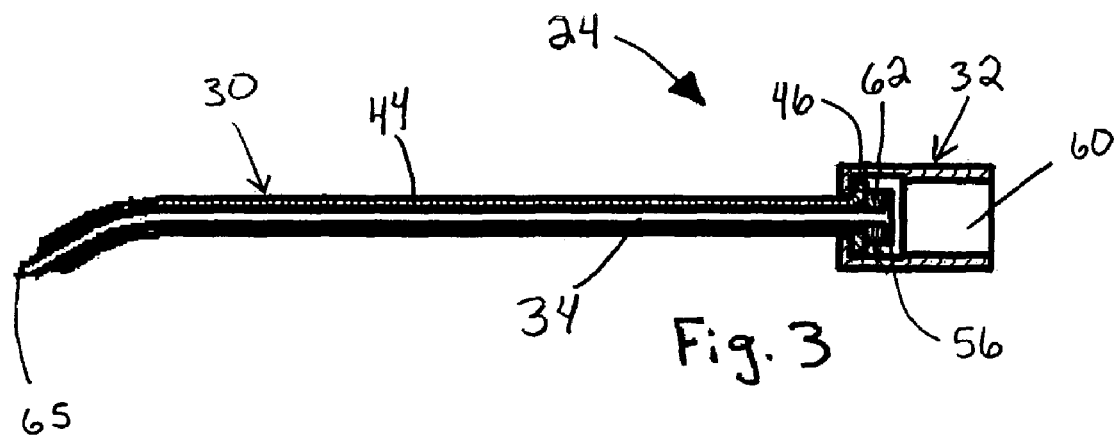
FIG. 3 is an assembled view of the microfracture pin assembly of FIG. 2.

Turning now to FIGS. 2 and 3, the microfracture pin assembly 24 is shown in more detail. As noted, the pin assembly 24 includes a guide tube 30, a connector 32, and a fracture pin 34. Tube 30 has an elongated cylindrical configuration with a body that extends from a proximal end 40 to a distal end 42. A cylindrical bore 44 extends completely through the body from the proximal to distal ends. The proximal end includes a head portion 46, and the distal end includes an angled tip 48.

Fracture pin 34 has an elongated cylindrical shape with a body that extends from a proximal end 50 to a distal end 52. The proximal end includes a head portion 56, and the distal end includes an angled tip 58. The fracture pin is sized and shaped to slideably fit into and move in bore 44 of guide tube 30.

Once assembled, the proximal ends of the guide tube and fracture pin are positioned in a cavity or recess 60 of connector 32. A spring or biasing member 62 is placed between the head 46 of the guide tube and the head 56 of the fracture pin. This biasing member provides the retraction force needed to withdraw the fracture pin from the bone and return the pin to the "ready" position in preparation for the next automated strike.

In operation, the piston (or other mechanism) of an automated orthopedic gun or instrument strikes the head 56 of the fracture pin. The fracture pin forceably moves down through the bore 44. As the pin moves, spring 62 compresses until the head 56 of the fracture pin and the head 46 of the guide tube are brought into close proximity of each other. Simultaneously, a sharp tip 65 of the fracture pin extends outwardly from the end of the guide tube.

Figure 4:
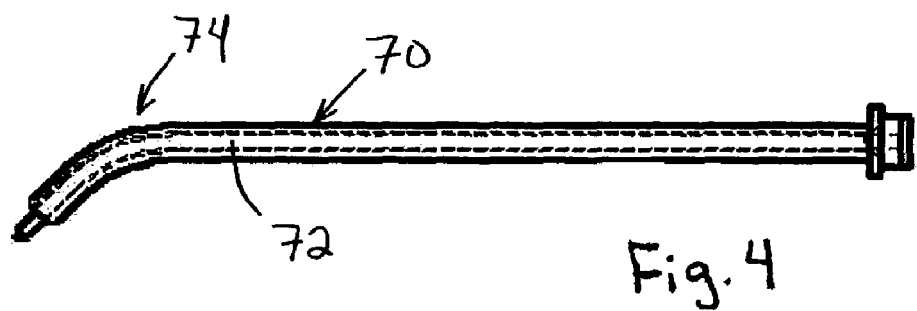
FIG. 4 is an alternate embodiment for a guide tube and fracture pin of the microfracture pin assembly.
Figure 5:
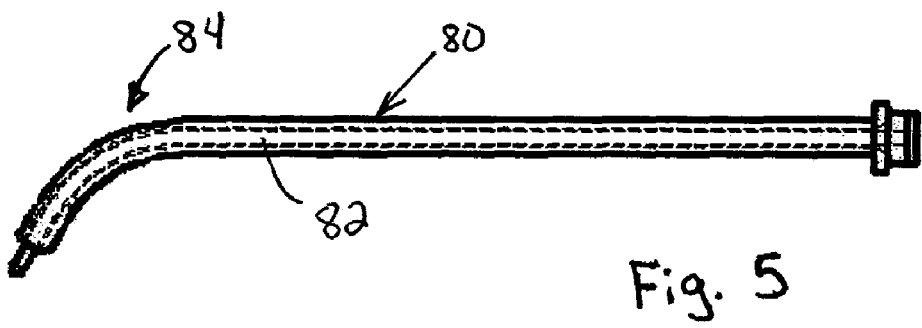
FIG. 5 is another alternate embodiment for a guide tube and fracture pin of the microfracture pin assembly.

As noted, the distal end 42 of the guide tube includes an angled tip 48. The angulation of this tip may vary. FIG. 3, for example, shows a 30° angle. FIG. 4 shows an alternate embodiment for the guide tube 70 and fracture pin 72 wherein the guide tube has an angled tip 74 with an angle of approximately 45°. FIG. 5 shows another alternate embodiment for the guide tube 80 and fracture pin 82 wherein the guide tube has an angled tip 84 with an angle of approximately 60°. Other angles are also within the scope of the invention. Guide tubes, for example, can be provided to have angled tips of various degrees between about 1° and 90°.

The microfracture pin assembly and the automated orthopedic gun or instrument can be designed to be disposable or re-useable. Further, one skilled in the art will appreciate that various materials can be used to fabricate the pin assembly and the automated orthopedic gun or instrument. The guide tube, for instance, can be made of polymer while the fracture pin is made of spring steel, Nitinol® or other acceptable and durable material and designed to be flexible and fracture resistant for the designed application and duration of use. Further yet, the spring can be formed as a coiled compression spring, a wave spring, rubber-like bumper spring, or other biasing member known in the art.

As another advantage of the present invention, the connector 32 is adapted to attached and detached from the microfracture inserter 10 (FIG. 1). As such, the guide tube, biasing member, and fracture pin can be easily changed during a microfracture procedure. Various guide tubes with different angled tips or different fracture pins can be used in the same procedure. The connector can be designed with a bayonet or similar type of quick-connect feature to aid the surgeon or assistant during changes of the tip and or guide tubes during the procedure During the microfracture surgical procedure, the microfracture instrument and microfracture pin assembly are used to create multiple holes or microfractures in the exposed subchondral bone plate. These holes can be formed in close proximity to each other. Preferably though, adjacent holes should not break into each other since the subchondral bone plate should not be damaged. Microfractured holes, for example, can be placed approximately 3 to 4 millimeters apart.

The depth of the holes can vary slightly, from about 2 to 4 millimeters. Generally, an adequate depth is reached when the subchondral bone plate is penetrated just enough to release fat droplets.

Another advantage of the present invention is that the microfracture pin assembly includes a stop mechanism designed to regulate and limit the depth at which the bone plate is penetrated. Looking to FIGS. 2 and 3, the depth of the microfractures is equal to the travel of the fracture pin 34 inside the guide tube 30. The fracture pin, though, is limited in movement or travel since it is designed to move down the guide tube a distance equal to the compression of the spring 62. In other words, as the spring compresses and the heads 56 and 46 move together, the fracture pin moves out from the distal end of the guide tube. The fracture pin is prevented from moving too far since head 46 of the guide tube will abut against head 56 and stop the fracture pin from moving. These two heads, thus, acts a safety mechanism and limit the amount of travel of the fracture pin.

Spring 62, then, can be sized and shaped and selected to have specific biasing properties so the fracture pin extends about 2 to 4 millimeters from the distal end of the guide tube when activated with the micro fracture instrument. Different springs can be used to vary the travel of the fracture pin and, thus, vary the depth of the microfractures in the bone plate.

Microfractures should first be placed around the periphery or edge of the defect and immediately adjacent to healthy cartilage rim. The holes can be placed in a peripheral pattern working towards the center of the defect.

The number and spacing of microfractures should be sufficient to establish a super clot. Such a clot will provide an optimal environment for a viable population of pluripotential marrow cells (messenchymal stem cells) to differentiate into stable tissue within the lesion or defect.

Another advantage of the present invention is that consistent and accurate spacing between adjacent microfractures can be obtained. The distal end 42 of the guide tube 30 can function as a guide for the placement of holes in the bone. In particular, the distal end of the guide has a diameter between about 6 to 8 millimeters. During the surgical procedure after a first hole is made in the subchondral bone plate, the guide tube is moved until the outer perimeter of the distal end is adjacent the perimeter of the first hole. A second hole can now be made with the edge of the guide tube adjacent the first hole. This second hole will be space about 3 to 4 millimeters (i.e., about one half of the diameter of the guide tube) from the first hole. In this manner, the surgeon ensures that successive holes are evenly spaced apart.

Guide tubes can be made to have different diameters to provide different spacing between adjacent holes. The different diameters can have a wide range, depending on the microfracture procedure and preferences of the surgeon.

Another important advantage of the present invention is that the microfractures are not manually made. Instead, the microfractures are formed with an automated process using, for example, the pneumatic instrument discussed in connection with FIG. 1. These microfractures can be quickly and easily created with a simple activation of the instrument. A surgeon merely pulls a trigger, pushes a button, steps on a control switch, or performs a similar task to activate movement of the fracture pin and create a microfracture in the bone plate. Successive microfractures are created with repeated activation of the instrument.

As yet another advantage of the present invention, the microfracture procedure of the present invention is simpler to perform. During some prior microfracture knee procedures, three arthroscopic portals were made in the skin of the patient. An arthroscopic camera was inserted into one port; a fluid management device was inserted into the second port; and microfracture instruments, such as awls or picks, were inserted through the third port. A primary assistant would hold the camera and pass instruments to the surgeon. The surgeon, in turn, needed two hands to create the microfractures: One hand held the awl, and one hand held the mallet to strike the awl. With the present invention, two hands are not required to create a microfracture. The surgeon can hold the pneumatic instrument with one hand and activate the instrument with the same hand or a foot. As such, the second hand of the surgeon can occupy another task, such as holding and manipulating the camera.

Once all of the microfractures are placed, the arthroscopic irrigation fluid pump pressure is reduced. Under direct visualization, the fat droplets and blood from the microfractured holes can be seen.

After the step of microfracturing the surface of subchondral bone is complete and the release of marrow is adequate, all instruments are removed from the knee. At this time, the joint is evacuated of fluid. No drains should be placed intra-articularly. A super clot rich in marrow elements should be allowed to form and stabilize while the lesion or defect is covered. The microfracture technique produces a rough surface in the lesion to which the clot can easily adhere while simultaneously maintaining the integrity of the subchondral plate for shaping the joint motion surface. At this time, it may also be appropriate for a protective, biologically compatible coating to be placed over the microfracture site. The purpose of such a coating would be to protect the clot site or even provide a culture bed for stimulating the growth of the repair cartilage. The arthroscopic ports are then closed.

This disclosure will not discuss in detail post-operative protocol or rehabilitation as such procedures are known in the art and tailored to meet the specific needs of the patient. Generally though, the rehabilitation should promote an environment for the pluripotential cells from the marrow to differentiate into articular cartilage cells. A healthy development of these cells will lead to the development and proliferation of durable cartilage that fills the original defect or lesion.

It should be emphasized that although the method of the present invention was described with a specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention.

Although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for performing microfracture surgery on subchondral bone in a knee to repair a full thickness chondral defect, the method comprising the steps of:
   establishing arthroscopic access to the knee;
   identifying the chondral defect in the knee;
   debriding the subchondral bone at the chondral defect;
   providing an automated microfracture inserter;
   creating multiple holes in the subchondral bone with the microfractured inserter;
   removing all instruments from the knee; and
   closing the arthroscopic access to the knee.

2. The method of claim 1 for performing microfracture surgery further comprising the step of activating the microfracture inserter to create one of the holes in the subchondral bone.

3. The method of claim 2 for performing microfracture surgery further comprising the step of activating the microfracture inserter once for each hole created in the subchondral bone.

4. The method of claim 1 for performing microfracture surgery further comprising the step of providing the microfracture inserter with a microfracture pin assembly that includes a fracture pin for creating the multiple holes in the subchondral bone.

5. The method of claim 4 for performing microfracture surgery further comprising the step of providing the pin assembly with a guide tube for guiding the fracture pin.

6. The method of claim 5 for performing microfracture surgery further comprising the step of providing the guide tube with an angled tip.

7. The method of claim 5 for performing microfracture surgery wherein the fracture pin is disposable.

8. A method for performing microfracture surgery on subchondral bone to repair a chondral defect, the method comprising the steps of:
   establishing arthroscopic access to the chondral defect;
   debriding the subchondral bone at the chondral defect;
   providing a pneumatic instrument;
   creating micro fractures in the subchondral bone with the pneumatic instrument; and
   closing the arthroscopic access to the chondral defect.

9. The method of claim 8 further comprising the step of providing the pneumatic instrument with a plurality of angled tips.

10. The method of claim 9 further comprising the step of providing the angled tips with a diameter of between 6 to 8 millimeters.

11. The method of claim 10 further comprising the step of providing the angled tips with angles from the group of angles of 30° 45° and 60°.

12. The method of claim 8 further comprising the step of providing the pneumatic instrument with a stop mechanism.

13. The method of claim 12 further comprising the step of limiting a depth of micro fractures in the subchondral bone.

14. The method of claim 13 further comprising the step of providing the pneumatic instrument with stop mechanism to perform the step of limiting a depth of microfractures in the subchondral bone.

15. The method of claim 14 further comprising the step of limiting the depth of microfractures from about 2 to 4 millimeters.

16. A method for performing microfracture surgery on subchondral bone to repair a chondral defect, the method comprising the steps of:
   establishing surgical access to the chondral defect;
   providing an automated orthopedic instrument;
   creating microfractured holes in the subchondral bone with the orthopedic instrument; and
   closing the surgical access to the chondral defect.

17. The method of claim 16 further comprising the steps of providing the orthopedic instrument with a fracture pin; and activating the orthopedic instrument to force the fracture pin against the subchondral bone to create the microfractured holes.

18. The method of claim 17 further comprising the step of limiting the depth of the microfractured holes in the subchondral bone to about 2 to 4 millimeters.

19. The method of claim 17 further comprising the step of providing a guide on the orthopedic instrument to space the microfractured holes about 3 to 4 millimeters apart.

20. The method of claim 17 further comprising the step of providing the fracture pin with a removable connection to the orthopedic instrument.

* * * * *